(12) United States Patent
Bammer et al.

(10) Patent No.: US 7,368,910 B2
(45) Date of Patent: May 6, 2008

(54) DUAL GRADIENT ECHO PULSE SEQUENCE USING INTERLEAVED SPIRAL-OUT SPIRAL-IN K-SPACE TRAJECTORIES

(75) Inventors: Roland Bammer, Palo Alto, CA (US); Michael Mosley, Redwood City, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 474 days.

(21) Appl. No.: 10/944,084

(22) Filed: Sep. 17, 2004

(65) Prior Publication Data

US 2006/0062731 A1    Mar. 23, 2006

(51) Int. Cl.
*G01V 3/00* (2006.01)
*A61B 5/055* (2006.01)

(52) U.S. Cl. .................. 324/306; 600/419; 600/420; 324/307; 324/309

(58) Field of Classification Search ........ 324/306–309, 324/318; 600/419, 420
See application file for complete search history.

(56) References Cited

U.S. PATENT DOCUMENTS

| | | | | |
|---|---|---|---|---|
| 5,122,747 A | * | 6/1992 | Riederer et al. | 324/309 |
| 5,270,653 A | * | 12/1993 | Pauly | 324/309 |
| 5,402,067 A | * | 3/1995 | Pauly et al. | 324/307 |
| 5,459,400 A | * | 10/1995 | Moonen | 324/309 |
| 5,485,086 A | * | 1/1996 | Meyer et al. | 324/307 |
| 5,539,313 A | * | 7/1996 | Meyer | 324/309 |
| 5,604,435 A | * | 2/1997 | Foo et al. | 324/309 |
| 5,652,516 A | * | 7/1997 | Adalsteinsson et al. | 324/309 |
| 6,400,151 B1 | * | 6/2002 | Haase et al. | 324/309 |
| 6,400,152 B1 | * | 6/2002 | Cline et al. | 324/309 |
| 6,556,009 B2 | * | 4/2003 | Kellman et al. | 324/309 |
| 6,853,191 B1 | * | 2/2005 | Miller et al. | 324/309 |
| 6,995,560 B2 | * | 2/2006 | Duerk et al. | 324/310 |
| 7,042,215 B2 | * | 5/2006 | Moriguchi et al. | 324/307 |
| 7,064,547 B1 | * | 6/2006 | King et al. | 324/309 |
| 7,078,899 B2 | * | 7/2006 | Dale et al. | 324/314 |
| 7,127,092 B2 | * | 10/2006 | Jack et al. | 382/128 |
| 2002/0002331 A1 | * | 1/2002 | Cline et al. | 600/410 |
| 2002/0097050 A1 | * | 7/2002 | Kellman et al. | 324/309 |
| 2003/0135105 A1 | * | 7/2003 | Jack et al. | 600/410 |
| 2003/0153826 A1 | * | 8/2003 | Jack et al. | 600/410 |
| 2005/0017717 A1 | * | 1/2005 | Duerk et al. | 324/307 |
| 2005/0033153 A1 | * | 2/2005 | Moriguchi et al. | 600/410 |
| 2006/0062731 A1 | * | 3/2006 | Bammer et al. | 424/9.3 |

OTHER PUBLICATIONS

Bammer, R. and Murray, K., "Improvements in SENSE MRI for Spiral and Echo-planar Imaging in Stroke," R01 Research Grant Proposal, Mar. 20, 2003.

(Continued)

*Primary Examiner*—Brij Shrivastav
*Assistant Examiner*—Tiffany A. Fetzner
(74) *Attorney, Agent, or Firm*—Beyer Law Group LLP

(57) ABSTRACT

Measurements of functional, hemographic, and blood flow parameters use a multiple echo or spin echo gradient pulse sequence whereby an early echo is acquired near the beginning of the pulse sequence which avoids saturation effects and a later echo near the end of the pulse sequence which can provide information with more sensitivity to a contrast agent for a susceptibility weighted image.

18 Claims, 2 Drawing Sheets

OTHER PUBLICATIONS

Bammer, Roland, "Improvements in SENSE MRI for Spiral and Echo-planar Imaging in Stroke," Grant No. 1R01EB002711-01, Abstract from http://crisp.cit.nih.gov/crisp/CRISP_LIB.getdoc?textkey=6735328&p_grant_num=1R01EB002711—01&p_query=&ticket=3908&p_audit_session_id=56809064&p_keywords=, downloaded on Jul. 30, 2004, 2 pages.

Pruessmann et al., "Advances in Sensitivity Encoding With Arbitrary k-space Trajectories," MRIM, vol. 46, pp. 638-651, 2001.

* cited by examiner

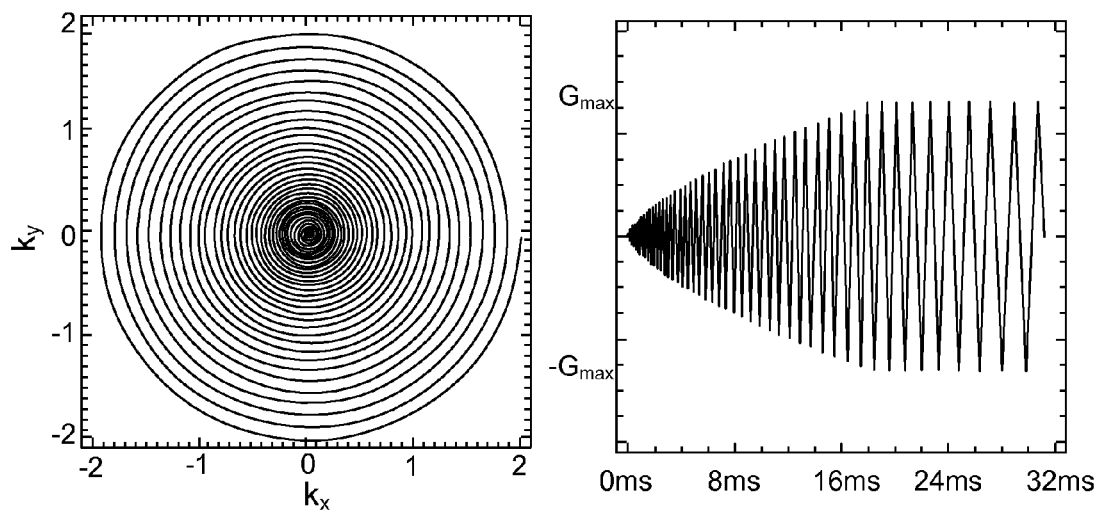
FIG. 1A
*(Prior Art)*
FIG. 1B
*(Prior Art)*
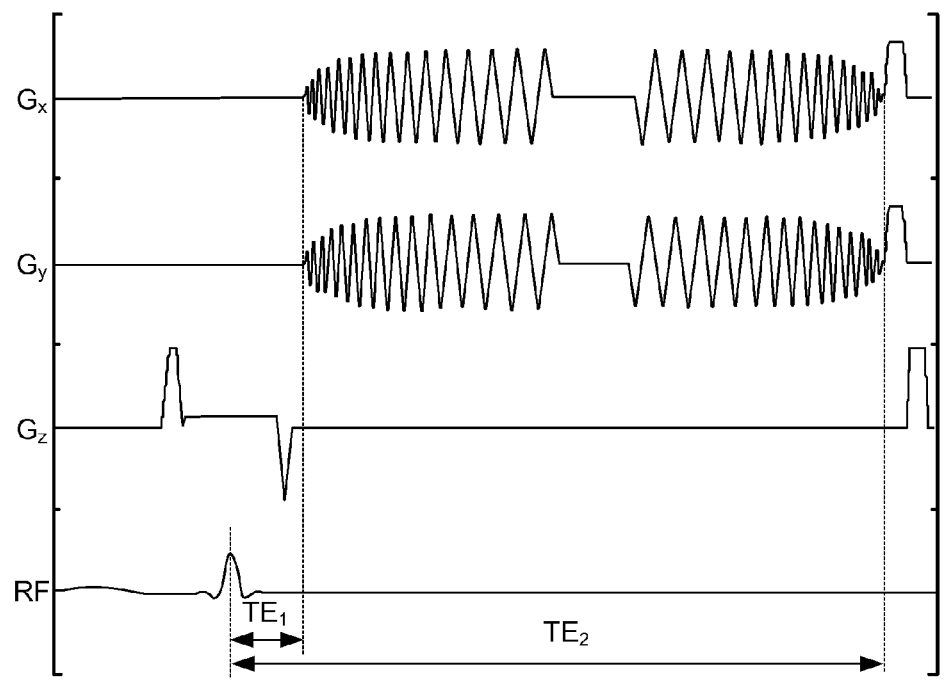
FIG. 2

DUAL GRADIENT ECHO PULSE SEQUENCE USING INTERLEAVED SPIRAL-OUT SPIRAL-IN K-SPACE TRAJECTORIES

GOVERNMENT RIGHTS

The U.S. government has rights to the disclosed invention pursuant to NIH Grant No. 1 R01 EB002711-01 to Stanford University on Sep. 26, 2003.

Attached hereto and incorporated by reference for all purposes is the Grant Application which was mailed to NIH on Mar. 21, 2003 for review.

BACKGROUND OF THE INVENTION

This invention relates generally to magnetic resonance imaging (MRI), and more particularly the invention relates to the use of MRI for the determination of hemodynamic parameters particularly in patients suffering from strokes.

Dynamic susceptibility contrast weighted (DSC) magnetic resonance perfusion imaging (PWI) promises to allow rapid assessment of hemodynamic parameters in stroke patients, which would allow better assessment of tissue viability and outcome prediction of stroke patient. In concert with diffusion weighted/diffusion tensor imaging, DWI/DTI, patients could be triaged on the basis of information derived from such quantitative perfusion measurements. This would have important implications for the treatment of stroke patients, since reperfusion therapy is only effective within the first few hours after the onset of stroke and can increase the mortality rate due to hemorrhagic transformation in later, more severe strokes. Unfortunately, in practice, DSC-PWI usually has limitations. Besides geometric distortions and poor resolution of EPI scans, there are considerable problems in accurately determining an arterial input function (AIF), which is required to determine the tissue residue function by deconvolving the tissue response signal with the AIF. Frequently, the internal carotid arteries (ICA) and parts of the initial branches of the anterior or the middle cerebral arteries (ACA, MCA) are difficult to depict or are contaminated by partial volume averaging.

The prior art suffers from strong signal saturation effects during the peak of the contrast agent bolus passage. Thus, the concentration of contrast material during this phase is underestimated and the arterial input function (AIF) that is deconvolved with the brain tissue response in each voxel is in error.

The present invention is directed to DSC-PWI with improved image quality and quantification capabilities.

SUMMARY OF THE INVENTION

The invention achieves measurements of functional, hemodynamic, and blood flow parameters by using a multiple echo or spin echo gradient pulse sequence whereby an early echo or spin echo is acquired at or near the beginning of the gradient pulse sequence and a later echo is acquired at or near the end of the gradient pulse sequence. The early echo avoids saturation effects and can provide spatial or temporal information of an arterial function, while the later echo can provide information with more sensitivity to a contrast agent for a susceptibility weighted image.

The gradient pulse sequence provides k-space trajectories that can over sample the origin of k-space and provide spatial and temporal RF coil sensitivity information which can be created from a simple short RF pulse or from interleaved multiple RF shots. The pulse sequence creates a refocused gradient echo which can be combined with a RF refocused spin echo. Alternatively, k-space sampling can be more dense away from k-space origin for use in functional MRI. T2 and T2* spatial and temporal measurements can be obtained. The T2 and T2* measurements can be acquired as a function of repetition times, TR, and used to eliminate confounding T1 relaxation effects.

In accordance with one embodiment of the invention, in dynamic susceptibility contrast based on perfusion imaging (DSC/PWI) the dual gradient echo MRI pulse sequence permits a better estimation of bolus passage of cerebral blood flow. The sequence includes a k-space trajectory with a dual echo interleaved spiral out-spiral with an early echo to improve the measurement of arterial input function (AIF) in carotid and cerebral arteries and a later second echo for image formation.

Advantageously, a minimum echo time (TE) is achieved for the first echo by using the spiral out trajectory while the spiral in trajectory allows complete image formation when the second echo is acquired.

The invention and objects and features thereof will be more fully understood from the following description and appended claims when taken with the drawings.

BRIEF DESCRIPTION OF THE DRAWINGS

FIGS. 1A, 1B illustrate k-space coverage and amplitude for a variable density spiral k-space trajectory as used in the invention.

FIG. 2 illustrates an imaging pulse sequence including a interleaved dual echo spiral out-spiral in trajecting in k-space as used in the invention.

DETAILED DESCRIPTION OF AN ILLUSTRATIVE EMBODIMENT

Figure 3:
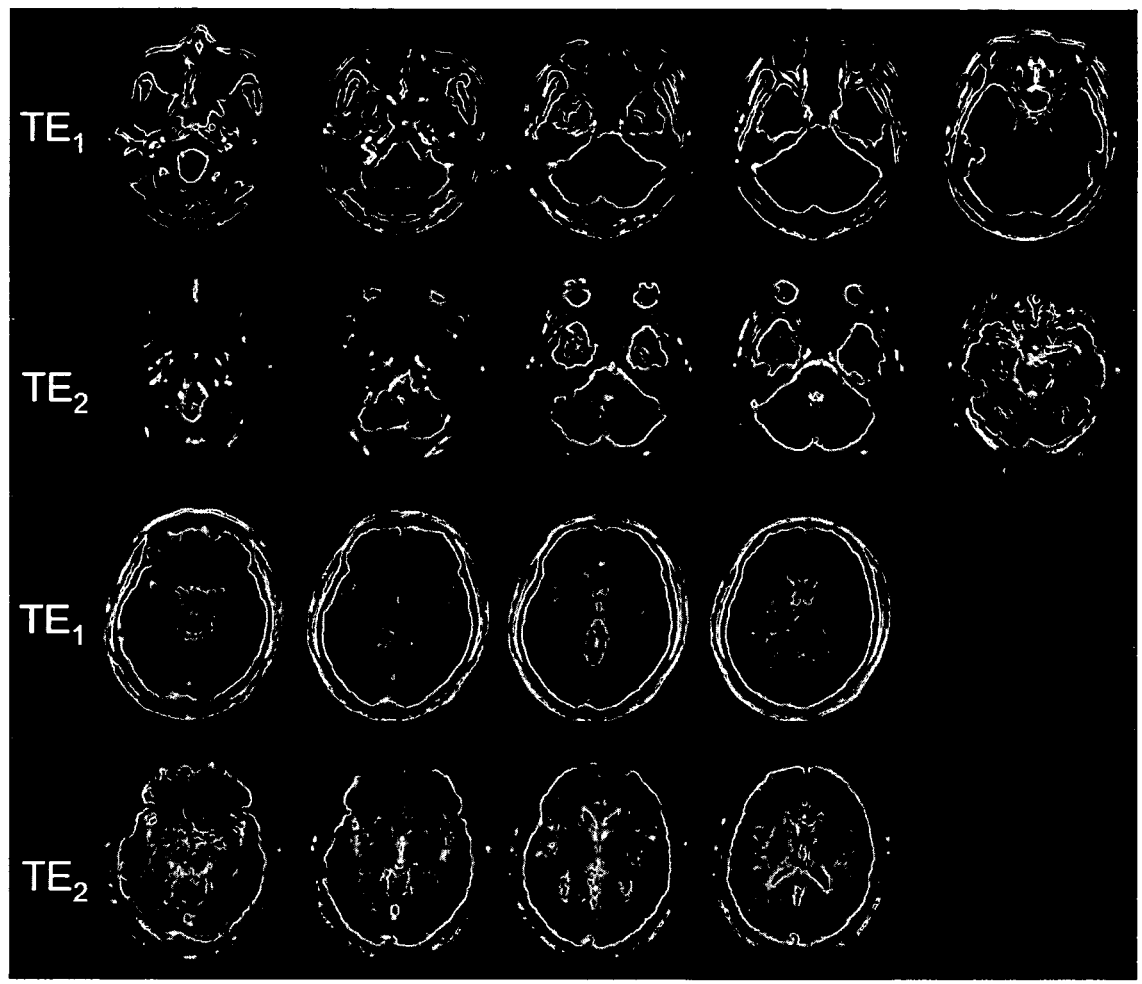
FIG. 3 is a series of images of the lower portion of a brain to demonstrate AIF measurements and imaging robustness against susceptibility distortions.

The invention will be described for an embodiment employing dynamic susceptibility contrast (DSC) based perfusion weighted imaging (PWI) of hemodynamic parameters, such as blood flow. More particularly, a dual gradient echo in accordance with the invention permits measurement of arterial input function (AIF) as well as image by employing sensitivity encoding (SENSE) signal acquisition.

Spiral imaging more efficiently uses gradient hardware compared to other fast imaging techniques and has the inherent advantage of gradient moment nulling. To increase spatial resolution and to reduce the influences from T2* decay, interleaved spiral trajectories that traverse quickly k-space are of great advantage. Since for each interleaf the k-space trajectory in spiral imaging is designed to start from the k-space origin, spiral imaging also provides inherent self-navigation capabilities. Spiral imaging also uses the available gradient power very effectively by distributing the load to at least two channels. It also has inherently dense sampling of the k-space origin, which provides phase navigation capabilities. Thus the diffusion-weighted spiral sequence based on a twice-refocused spin echo sequence in accordance with the invention has advantages in imaging hemodynamic parameters.

T2* driven susceptibility contrast (DSC)-based PWI is most often performed using single-short echo planar (EPI) readout. However, the determination of hemodynamic parameters, such as cerebral blood flow, is challenged by technical difficulties. Besides the strong geometric distortions and poor resolution of EPI scans, there are considerable problems in determining accurately an arterial input function (AIF), which is mandatory for deconvolving the tissue response signal. Using single-shot EPI, large feeding vessels, such as the internal carotid arteries (ICA) or branches of the major cerebral arteries, are frequently difficult to depict and can be contaminated by tissue partial volume averaging. This is mainly due to strong $T2^*$-induced blurring, susceptibility gradients emanating from the sinuses and the auditory canals adjacent to the brain, and the high concentration of contrast material during bolus passage that causes clipping of the bolus maximum due to the lack of dynamic range and low SNR. These problems are minimized by using a dual-echo acquisition in combination with a multi-shot sensitivity-encoded variable-density interleaved spiral imaging approach, in accordance with the invention.

A multi-slice DSC-PWI pulse sequence was implemented with interleaved variable-density spiral readout gradients where the center of k-space was sampled with sufficient density for estimation of the coil sensitivities and for phase-navigation. FIG. 1 illustrates a variable density spiral design with one interleave of a 4 interleaf VD spiral scan. The k-space coverage at the origin is considerable higher than at the outer portion of k-space. Corresponding gradient-waveform that is played out on the x-gradient coil. At the beginning, the gradient-waveform starts in the slew-rate limited mode. After it reaches the maximum amplitude (determined by the FOV and the maximum available sampling rate) it changes to the gradient-amplitude limited regime. For high scan efficiency, a spiral-out/in trajectory was used. FIG. 2 illustrates and interleaved dual-echo spiral-out spiral in imaging pulse sequence. One interleaved spiral-out scan guarantees an early echo to improve the measurement of AIF in ICA, MCA, or ACA. The spiral-in part enables the most compact acquisition since the image formation is finished when the second echo is acquired. For each spiral, a SENSE reduction factor of 2.0 is used along the radial dimension. To avoid hysteresis effects, the spiral-out trajectory (early echo) was the time-reversed version of the spiral-in waveform. This design gives a minimum TE for the early echo minimum TE for the early echo (TE1=6 ms) (spiral-out) while producing enough $T2^*$-effect in the feeding arteries without severe geometric distortions or saturation effects 3. The spiral-in trajectory guarantees that the image formation is finished at the late echo time (TE2=55 ms), providing the most effective readout while still sufficiently sensitive to detect the subtle contrast passage in deep white matter. Calculating $DR2^*$ from the two echoes helps to avoid T1-effects.

All MR scans were performed on a 1.5T MRI scanner (Signa CV/i, GE Medical Systems, Waukesha, Wis.) fitted with high performance gradients (40 mT/m, $t_{rise}$=268 µs) and a four-element phased array coil. All procedures were approved by the institutional review board of our institution. The dual-echo spiral sequence was implemented using the following parameters: FOV=22 cm, 5 mm/1 mm section thickness/gap, 20 slices, $TR/TE_1/TE_2/\alpha$=500 ms/6 ms/55 ms/45°, reconstruction matrix 128×128, bandwidth ±100 kHz, four interleaves, dynamic scan resolution=2 s, and 80 time points. To reduce geometric distortions from off-resonant spins, a SENSE reduction factor of 2.0 was introduced along the radial dimension of the trajectory. An iterative generalized SENSE (GSENSE) algorithm was used to reconstruct the undersampled spiral trajectories. Coil sensitivity information was retrieved from the center portion of each interleave.

Spiral MRI uses the available gradient power effectively by distributing the load to at least two gradient channels. The variable density approach uses increased sampling near to the k-space origin, which enables phase navigation and auto-calibration (GSENSE) capabilities; this minimizes motion sensitivity of the sequence and the SENSE reconstruction process. FIG. 3 shows a series of images that were acquired using the new dual-echo spiral sequence The pulse sequence of FIG. 2 was applied at lower levels of the brain to demonstrate its great potential for AIF measurements without significant distortions. At the early echo image all major vessels could be clearly delineated and show less contamination from partial volume effects due to reduced blurring and smaller voxel size. The late echo provides sufficient $T2^*$-sensitivity to detect signal changes in the parenchymal microvasculature during bolus passage. Overall, the interleaved regime significantly reduced geometric distortions around areas with large susceptibility gradients.

The lower portion of the head was scanned to demonstrate the robustness against susceptibility distortions. When compared to conventional single-shot EPI, the interleaved spiral approach combined with GSENSE allowed a significant reduction of distortions from off-resonant spins. Specifically, the regions adjacent to sinuses and the auditory canals were well preserved. The large feeding vessels can be clearly delineated and the typical $T2^*$-"blooming" effect during bolus passage can be avoided. In contrast to single-shot EPI, where pixel shifts (of voxels containing large amounts of Gd) along the phase-encode direction due to the low bandwidth per pixel can be quite significant and may lead to perturbed AIF shapes, the interleaved spiral approach is much more immune against such distortions. Due to the short readouts and the fact that the acquisition is finished almost immediately after the second echo (FIG. 2), the sequence is very efficient and allows full brain coverage.

The interleaved dual-echo spiral-out-spiral-in approach combined with GSENSE provides significantly improved image quality, better spatial resolution, and, hence, better vessel conspicuity. These improvements allow one to perform more reliable measurements of the AIF, while still being sufficiently sensitive to small $T2^*$-changes in white matter. In addition, quantitative $\Delta R2^*$-maps, calculated from the two echoes, account for T1-effects, which is important especially at shorter TRs and for time points after the initial bolus passage.

While the invention has been described with reference to a specific embodiment, the description is illustrative of the invention and not limiting the invention. Various applications and modifications, as noted above, may occur to those skilled in the art without departing from the true spirit and scope of the invention as defined by the appended claims.

What is claimed is:

1. A method of magnetic resonance imaging of hemodynamic or blood flow parameters comprising the steps of:
   a) applying pulse echo RF excitation pulses to excite nuclear spins,
   b) applying a multiple gradient or spin echo pulse sequence whereby an early echo is acquired near the beginning of the pulse sequence and a later echo is acquired near the end of the gradient pulse sequence, and
   c) using echo signals to derive spatial and temporal maps of quantitative functional, hemodynamic, or blood flow parameters, wherein the gradient pulse sequence provides k-space trajectories that oversample the origin of k-space and provide spatial and temporal RF coil sensitivities information for use in parallel image reconstruction and wherein the early echo avoids saturation effects and provides a spatial or temporal information of an arterial input function, and the later echo provides information with more sensitivity to a contrast agent for a susceptibility weighted image.

2. The method of claim 1 as applied for use in dynamic susceptibility contrast (DSC) perfusion weighted imaging (PWI).

3. The method of claim 1 wherein k-space sampling is dense near k-space origin as applied for phase or motion navigation for motion sensitive imaging.

4. The method of claim 1 wherein k-space sampling is dense away from k-space origin as applied to functional MRI.

5. The method of claim 1 wherein the k-space origin is sufficiently densely sampled to derive coil weights required for k-space based parallel imaging techniques.

6. The method of claim 5 wherein spatial and temporal changes in coil sensitivity from coil motion or body motion from shot to shot are derived.

7. The method of claim 1 wherein quantitative T2* spatial and temporal measurements are obtained.

8. The method of claim 7 wherein the measurements are used to derive quantitative functional, hemodynamic, or blood flow information.

9. The method of claim 1 wherein quantitative T2 spatial and temporal measurements are obtained.

10. The method of claim 1 wherein T2 or T2* spatial and temporal measurements are acquired as a function of repetition time TR, and are used to eliminate confounding T1 relaxation effects.

11. The method of claim 1 wherein the information is acquired by control of a spin echo or a gradient echo to derive spatial and temporal information to differentiate between large blood vessel and small blood vessel data contributions to the quantitative functional, hemodynamic, or blood flow information.

12. The method of claim 1 wherein the information is acquired by control of a spin echo or a gradient echo to derive coherent and incoherent quantitative information to differentiate between large blood vessel and small blood vessel data contributions.

13. The method of claim 1 wherein the dual gradient pulse sequence traverses a k-space trajectory in interleaved spiral out-spiral in paths to create a refocused gradient echo which can be combined with a RF refocused spin echo.

14. The method of claim 13 wherein the pulse sequence is repeated with variable density trajectories.

15. The method of claim 13 wherein images can be created from a single shot RF pulse or from interleaved multiple RF shots.

16. The method of claim 13 wherein the k-space trajectories provide self navigating.

17. The method of claim 13 wherein the pulse sequence is used to acquire separately spaced even echoes to derive rephased functional, hemodynamic, or blood flow information.

18. The method of claim 1 wherein the k-space origin is sufficiently densely sampled to create low resolution imaging from which spatial and temporal RF coil sensitivities can be derived.

* * * * *

UNITED STATES PATENT AND TRADEMARK OFFICE
CERTIFICATE OF CORRECTION

| | | |
|---|---|---|
| PATENT NO. | : 7,368,910 B2 | Page 1 of 1 |
| APPLICATION NO. | : 10/944084 | |
| DATED | : May 6, 2008 | |
| INVENTOR(S) | : Bammer et al. | |

It is certified that error appears in the above-identified patent and that said Letters Patent is hereby corrected as shown below:

In The Specification Under Column 1:

• Please replace lines 5-12 with:

--FEDERALLY-SPONSORED RESEARCH OR DEVELOPMENT
This invention was made with Government support under contracts EB002711, NS035959, NS039325, and RR009784 awarded by the National Institutes of Health. The Government has certain rights in this invention.--

Signed and Sealed this

Nineteenth Day of April, 2011

David J. Kappos
*Director of the United States Patent and Trademark Office*